(12) United States Patent
Blanchard et al.

(10) Patent No.: US 12,367,751 B2
(45) Date of Patent: Jul. 22, 2025

(54) ALERT SYSTEM

(71) Applicant: MY MEDIC WATCH PTY LTD, Sydney (AU)

(72) Inventors: Elizabeth Blanchard, Sydney (AU); Laurent Parsy, Sydney (AU); Bruce Brew, Sydney (AU); Helene Blanchard, Sydney (AU); Andreanne Blanchard, Sydney (AU); Serge Lauriou, Sydney (AU)

(73) Assignee: MY MEDIC WATCH PTY LTD, Sydney (AU)

( * ) Notice: Subject to any disclaimer, the term of this patent is extended or adjusted under 35 U.S.C. 154(b) by 961 days.

(21) Appl. No.: 17/320,801

(22) Filed: May 14, 2021

(65) Prior Publication Data

US 2021/0295668 A1    Sep. 23, 2021

Related U.S. Application Data

(63) Continuation-in-part of application No. 16/339,220, filed as application No. PCT/AU2017/000209 on Oct. 5, 2017, now abandoned.

(30) Foreign Application Priority Data

Oct. 5, 2016    (AU) ................................ 2016904045

(51) Int. Cl.
*G08B 21/04*    (2006.01)
*A61B 5/00*    (2006.01)
(Continued)

(52) U.S. Cl.
CPC .......... *G08B 21/043* (2013.01); *A61B 5/1117* (2013.01); *A61B 5/4094* (2013.01);
(Continued)

(58) Field of Classification Search
None
See application file for complete search history.

(56) References Cited

U.S. PATENT DOCUMENTS 8,773,269 B2 * 7/2014 Richardson ............ A61B 5/411
340/539.11
8,933,801 B2 * 1/2015 Sweeney ............... G08B 21/043
600/595
(Continued)

FOREIGN PATENT DOCUMENTS

CN    104771177 A    7/2015
JP    4357302 B2    7/2005
(Continued)

*Primary Examiner* — Michael R Bloch
(74) *Attorney, Agent, or Firm* — Hayes Soloway P.C.

(57) ABSTRACT

A system is provided which, in at least some embodiments, can read the vital signs of the body of a user utilizing a sensing device such as a smartwatch or smart phone (for example utilizing the IOS, Android or Pebble operating systems) and apply algorithms to interpret the vital signs and then send a notification with an escalation process to nominated carriers if the patient is interpreted as having a fall or fit or seizure. In at least some embodiments doctors or other parties can log in to a secured dashboard and check a patient data in real time. Doctors or other parties can analyze the history of the patient. In at least some embodiments, users/patients can also use data to keep track of fall or fit or seizure episodes and monitor their progress.

11 Claims, 13 Drawing Sheets

(51) Int. Cl.
  *A61B 5/11* (2006.01)
  *G06N 20/00* (2019.01)
  *G08B 29/18* (2006.01)

(52) U.S. Cl.
  CPC ............ *A61B 5/681* (2013.01); *G06N 20/00* (2019.01); *G08B 21/0446* (2013.01); *G08B 29/185* (2013.01)

(56) References Cited

U.S. PATENT DOCUMENTS

| | | |
|---|---|---|
| 9,689,887 B1 | 6/2017 | Srinivas et al. |
| 2006/0282021 A1* | 12/2006 | DeVaul ............... A61B 5/0205 600/595 |
| 2008/0129518 A1* | 6/2008 | Carlton-Foss ....... G08B 25/009 379/45 |
| 2013/0116514 A1 | 5/2013 | Kroner et al. |
| 2015/0130613 A1 | 5/2015 | Fullam |
| 2015/0269826 A1 | 9/2015 | Zhang et al. |
| 2015/0282717 A1 | 10/2015 | McCombie et al. |

FOREIGN PATENT DOCUMENTS

| | | | |
|---|---|---|---|
| JP | 2005278765 A | 10/2005 | |
| JP | 2013000311 A | 1/2013 | |
| JP | 2016508039 A | 3/2016 | |
| KR | 20100000317 A | 1/2010 | |
| WO | 2006101587 A2 | 9/2006 | |

\* cited by examiner

ALERT SYSTEM

CROSS-REFERENCE TO RELATED APPLICATIONS AND PRIORITY

This patent application is a Continuation-in-Part of U.S. patent application Ser. No. 16/339,220 filed Apr. 3, 2019, which claims priority from PCT Patent Application No. PCT/AU2017/000209 filed Oct. 5, 2017, which claims priority from Australian Patent Application No. 2016904045 filed Oct. 5, 2016. Each of these patent applications are herein incorporated by reference in their entirety.

TECHNICAL FIELD

The present invention relates to an alert system and, more particularly although not exclusively, to such a system adapted, although not exclusively, to assist in the management of people who may be prone to falling, whether by medical condition, age or otherwise.

BACKGROUND

To date, systems which monitor people have not been specifically adapted to detect selected conditions including one or more of specific conditions such as a fall condition, a seizure or a sleepwalk event, or related events, to systematically analyze the event and communicate the event both locally and to a remote location. U.S. Pat. No. 9,689,887 assigned to Amazon Technologies describes a methodology for detecting a fall event associated with a parcel or the like.

However, detection of a fall condition of a human body requires a different approach because of the complexity and variation of the manner in which a human may fall to the ground.

In particular forms, the primary sensing will be carried out by a body-worn sensor and more particularly a limb mounted sensor and more particularly a wrist mounted sensor. Again, there is complexity associated with using a limb to sense movement pertinent to the entire human body.

It is an object of the present disclosure to address or at least ameliorate some of the above disadvantages.

It will also be advantageous if the alert system can be adapted to sense, analyze and communicate other conditions instead of or in addition to the fall condition referenced above thereby to provide a multifunctional alert system.

Notes

The term "comprising" (and grammatical variations thereof) is used in this specification in the inclusive sense of "having" or "including," and not in the exclusive sense of "consisting only of."

The above discussion of the prior art in the Background of the disclosure is not an admission that any information discussed therein is citable prior art or part of the common general knowledge of persons skilled in the art in any country.

SUMMARY OF INVENTION

Definitions

In this disclosure, a body-worn sensor or wearable device sensor is a sensor which is mechanically associated with the body of a user such that the sensor can sense at least acceleration of the body relative to a reference frame. In particular forms the primary sensing for embodiments of the present disclosure will be carried out by a body-worn sensor and more particularly a limb mounted sensor and more particularly a wrist mounted sensor.

In this disclosure, a reference frame is a reference frame pertinent to sensing of acceleration of the body. In some instances, the reference frame will be the surface upon which the user is supported. In some instances, the reference frame will be the earth. In the case where the user is already moving with respect to the earth, for example where they are in a lift or an aeroplane or other moving vehicle, the reference frame will be that lift or aeroplane or vehicle and more particularly the surface within that vehicle or lift or aeroplane upon which the user is supported.

Accordingly, in one broad form of the present disclosure there is provided an alert system for communicating an event sensed by a body worn sensor.

In some embodiments, the body-worn sensor is mechanically associated with the body.

In some embodiments, the event is a fall event.

In some embodiments, the sensor may include a processor in communication with memory for on-board processing of at least one signal.

In some embodiments, the sensor may include a timer.

In some embodiments, the sensor may include a GPS device.

In some embodiments, the sensor may include a communications device.

In some embodiments, the communications device may include broadband network interconnectivity for connection to the Internet.

In some embodiments, the communications device includes cellular telephone network interconnectivity for connection of the device to a local cellular telephone network.

In some embodiments, the sensor may include an accelerometer.

In some embodiments, the at least one signal is an acceleration signal.

In some embodiments, the at least one signal is a timing signal.

In some embodiments, the signal is an acceleration signal derived from the accelerometer.

In some embodiments, the signal is a timing signal derived from the timer.

In some embodiments, the signal is a GPS signal derived from the GPS device.

In some embodiments, the event is a fall event.

In some embodiments, the event is a seizure event.

In some embodiments, the event is a sleepwalk event.

In some embodiments, the system may further include an additional monitoring or sensing device.

In these and other embodiments, the additional monitoring or sensing device may include at least a speaker and a microphone and may be in communication with a web-enabled server.

In these and other embodiments, the web-enabled server may execute an application whereby functionality of the body-worn sensor is supplemented with the functionality of the additional monitoring or sensing device.

In some embodiments, the body-worn sensor may be mounted to the wrist of a user.

In some embodiments, an artificial intelligence AI capability may be programmed into a memory of the sensor for execution by a processor of the body-worn sensor.

In some embodiments, an AI program may be executed on the processor associated with server located remote from the sensor.

In some embodiments, the AI capability may learn from false positive event determination and false negative event determination in order to statistically improve reliability of detection of an event over time and with particular reference to learned attributes of the data associated with any given user.

In a further broad form of the present disclosure there is provided a fall detection apparatus comprising:
  an accelerometer which communicates an acceleration signal to a processor,
  the acceleration signal quantifying acceleration on a substantially continuous basis relative to a reference frame;
  a timer which communicates a time reference signal to the processor, the processor monitoring the acceleration signal and timing signal on a substantially continuous basis, whereby if the acceleration signal is within a first low acceleration range for a predetermined period of time and is followed by a second high acceleration signal in a second predetermined period of time a fall condition is determined by the processor.

In some embodiments, the processor may monitor the timing signal and the acceleration signal during a third predetermined period of time subsequent to the second predetermined period of time, whereby if the acceleration signal remains in a predetermined very low range during the third predetermined period of time, then it is determined that the user is immobile and a fall detection event is confirmed.

In some embodiments, when a fall condition is determined by the processor a fall signal may be transmitted to a remote location.

In some embodiments, when a fall condition is determined by the processor, a fall signal may be communicated locally.

In some embodiments, the acceleration signal may be referenced against a reference frame.

In some embodiments, the reference frame is the surface upon which a user of the fall detection apparatus is supported.

In some embodiments, the fall detection apparatus is a wrist-mounted fall detection apparatus.

In a further broad form of the present disclosure there is provided a detection and communication system which reads vital signs of the body of a user utilizing a sensing device and applies algorithms to interpret the vital signs and then sends a notification with an escalation process to nominated carriers if the user is interpreted as having a fall or fit or seizure.

In some embodiments, the device is a smartwatch or smart phone (for example utilising the IOS, ANDROID or Tizen operating systems).

In some embodiments, doctors or other parties can log in to a secured dashboard and check user data in real time.

In some embodiments, doctors or other parties can analyze the history of the user.

In some embodiments, users/patients can also utilize user data derived by the system to keep track of fall or fit or seizure episodes and monitor their progress.

In yet a further broad form of the present disclosure there is provided a seizure detection apparatus comprising:
  an accelerometer which communicates an acceleration signal to a processor, the acceleration signal quantifying acceleration on a substantially continuous basis relative to a reference frame;
  a timer which communicates a time reference signal to the processor, the processor monitoring the acceleration signal and timing signal on a substantially continuous basis, whereby if the acceleration signal oscillates within a predetermined range for a predetermined period of time then a seizure event is determined and signalled.

In some embodiments, the seizure detection apparatus is a wrist-mounted seizure detection apparatus.

In yet a further broad form of the present disclosure there is provided a sleepwalk detection apparatus comprising:
  an accelerometer which communicates an acceleration signal to a processor, the acceleration signal quantifying acceleration on a substantially continuous basis relative to a reference frame;
  a timer which communicates a time reference signal to the processor;
  the processor monitoring the acceleration signal and the timing signal on a substantially continuous basis, whereby if the acceleration signal indicates a walking movement during a predetermined period of time which exceeds a minimum walking time and which is determined to be a bed time of the user then a sleepwalk event is determined and signaled.

In some embodiments, the sleepwalk detection apparatus is a wrist-mounted sleepwalk detection apparatus.

In yet a further broad form of the present disclosure there is provided a method of detecting a fall event comprising:
  providing an accelerometer which communicates an acceleration signal to a processor, the acceleration signal quantifying acceleration on a substantially continuous basis relative to a reference frame;
  providing a timer which communicates a time reference signal to the processor, the processor monitoring the acceleration signal and the timing signal on a substantially continuous basis, whereby if the acceleration signal is within a first low acceleration range for a predetermined period of time and is followed by a second high acceleration signal in a second predetermined period of time a fall condition is determined by the processor.

In yet a further broad form of the invention there is provided a method of seizure detection comprising:
  providing an accelerometer which communicates an acceleration signal to a processor; the acceleration signal quantifying acceleration on a substantially continuous basis relative to a reference frame;
  providing a timer which communicates a time reference signal to the processor;
  the processor monitoring the acceleration signal on a substantially continuous basis;
  the processor monitoring the timing signal on a substantially continuous basis;
  and whereby if the acceleration signal oscillates within a predetermined range for a predetermined period of time then a seizure event is determined and signalled.

In yet a further broad form of the present disclosure there is provided a method of detecting a sleepwalk event comprising:
  providing an accelerometer which communicates an acceleration signal to a processor, the acceleration signal quantifying acceleration on a substantially continuous basis relative to a reference frame;
  providing a timer which communicates a time reference signal to the processor, the processor monitoring the acceleration signal and the timing signal on a substantially continuous basis, whereby if the acceleration signal indicates a walking movement during a predetermined period of time which exceeds a minimum walking time and which is determined to be a bed time of the user then a sleepwalk event is determined and signalled.

In yet a further broad form of the present disclosure there is provided a fall detection apparatus comprising:
an accelerometer which communicates an acceleration signal to a processor, the acceleration signal quantifying acceleration on a substantially continuous basis relative to a reference frame;
a timer which communicates a time reference signal to the processor, the processor monitoring the acceleration signal and the time reference signal on a substantially continuous basis, the processor waiting for the acceleration signal to indicate low acceleration within a first low acceleration range, wherein when the acceleration signal is within the first low acceleration range for a predetermined first period of time comprising a waiting for low acceleration step and is followed by a second high acceleration signal in a second high acceleration range in a second predetermined period of time comprising a waiting for high acceleration step a fall condition is determined by the processor, wherein the processor monitors the time reference signal and the acceleration signal during a third predetermined period of time subsequent to the second predetermined period of time whereby if the acceleration signal remains in a predetermined very low acceleration range during the third predetermined period of time comprising a calculating if the user stays immobile on the surface step, wherein the predetermined very low acceleration range comprises the acceleration signal being lower than an on the ground acceleration sensitivity setting during a time to detect on the floor time setting within a time on the floor time setting then it is determined that a user is immobile on the surface and a fall detection event is confirmed, and wherein a plurality of parameters of each of the first low acceleration range, the second high acceleration signal and the predetermined very low acceleration range are customised for each user with reference to personal profile settings unique to each said user and can be updated by the user.

In yet a further broad form of the present disclosure there is provided a method of detecting a fall event comprising:
providing an accelerometer which communicates an acceleration signal to a processor, the acceleration signal quantifying acceleration on a substantially continuous basis relative to a reference frame;
providing a timer which communicates a time reference signal to the processor; the processor monitoring the acceleration signal and the time reference signal on a substantially continuous basis;
waiting for the acceleration signal to indicate low acceleration within a first low acceleration range, wherein when the acceleration signal is within the first low acceleration range for a predetermined first period of time comprising a waiting for low acceleration step and is followed by a second high acceleration signal in a second high acceleration range in a second predetermined period of time comprising a waiting for high acceleration step a fall condition is determined by the processor, wherein the processor monitors the time reference signal and the acceleration signal during a third predetermined period of time subsequent to the second predetermined period of time whereby if the acceleration signal remains in a predetermined very low acceleration range during the third predetermined period of time comprising a calculating if the user stays immobile on the surface step, wherein the predetermined very low acceleration range comprises the acceleration signal being lower than an on the ground acceleration sensitivity setting during a time to detect on the floor time setting within a time on the floor time setting then it is determined that a user is immobile on the surface and a fall detection event is confirmed, and wherein a plurality of parameters of each of the first low acceleration range, the second high acceleration signal and the predetermined very low acceleration range are customized for each user with reference to personal profile settings unique to each said user and can be updated by the user.

In yet a further broad form of the present disclosure there is provided a detection and communication system which utilizes the method as described above to detect a fall condition and confirm a fall detection event, said system utilizing a method of detecting the fall event comprising:
providing an accelerometer which communicates an acceleration signal to a processor, the acceleration signal quantifying acceleration on a substantially continuous basis relative to a reference frame;
providing a timer which communicates a time reference signal to the processor, the processor monitoring the acceleration signal and the time reference signal on a substantially continuous basis;
waiting for the acceleration signal to indicate low acceleration within a first low acceleration range, wherein when the acceleration signal is within the first low acceleration range for a predetermined first period of time and is followed by a second high acceleration signal in a second predetermined period of time a fall condition is determined by the processor, wherein the processor monitors the time reference signal and the acceleration signal during a third predetermined period of time subsequent to the second predetermined period of time, whereby if the acceleration signal remains in a predetermined very low acceleration range during the third predetermined period of time then it is determined that a user is immobile and the fall detection event is confirmed, said system reading a plurality of vital signs of a body of the user utilizing a sensing device in a form of a body-worn sensor and applies algorithms to interpret whether the fall detection event has occurred and then send a notification of the fall detection event with an escalation process to nominated carriers by way of a server incorporating a separate processor if the user is interpreted as having a fall, said system implemented by means of the processor associated with the body-worn sensor and the separate processor associated with the server.

In a further broad form of the present disclosure there is provided a fall detection apparatus comprising:
an accelerometer which communicates an acceleration signal to a processor, the acceleration signal quantifying acceleration on a substantially continuous basis relative to a reference frame;
a timer which communicates a time reference signal to the processor, the processor monitoring the acceleration signal and the time reference signal on a substantially continuous basis, the processor waiting for the acceleration signal to indicate low acceleration within a first low acceleration range, wherein when the acceleration signal is within the first low acceleration range for a predetermined first period of time comprising a waiting for low acceleration step and is followed by a second high acceleration signal in a second high acceleration range in a second predetermined period of time comprising a waiting for high acceleration step a fall condition is determined by the processor, wherein the processor monitors the time reference signal and the acceleration signal during a third predetermined period of time subsequent to the second predetermined period of time, whereby if the acceleration signal remains in a predetermined very low acceleration range during the third predetermined period of time comprising a calculating if the user stays immobile on the surface step, wherein the predetermined very low acceleration range comprises the acceleration signal being lower than an On The Ground acceleration Sensitivity setting during a Time To Detect On The Floor time setting and wherein the sum of the Time On The Floor periods is greater than the Time On The Floor setting then it is determined that a user is immobile on the surface and a fall detection event is confirmed, and wherein a plurality of parameters of each of the first low acceleration range, the second high acceleration signal and the predetermined very low acceleration range are customized for each user with reference to personal profile settings unique to each said user and can be updated by the user.

In some embodiments, when the fall detection event is confirmed by the processor a fall signal may be transmitted by a transmitter to a remote location.

In some embodiments, when the fall detection event is confirmed by the processor, a fall signal may be communicated locally.

In some embodiments, the acceleration signal may be referenced against the reference frame.

In some embodiments, the reference frame is a surface upon which the user of the fall detection apparatus is supported.

In some embodiments, the fall detection apparatus may be a wrist-mounted fall detection apparatus.

In some embodiments, a weighting system receives from a mobile app 461 executed on a portable digital device 460 providing input 470 from a Threshold-Based Algorithm (TBA) 401 and input from a Machine Learning Model (MLM) 402; the weighting system 404 varying the weight applied to the respective inputs over time thereby to increase reliability of fall detection decisions.

In some embodiments, said Time To Detect On The Floor excludes time when the acceleration signal is greater than the On The Ground acceleration Sensitivity setting.

In a further broad form of the present disclosure there is provided a method of detecting a fall event comprising:
providing an accelerometer which communicates an acceleration signal to a processor, the acceleration signal quantifying acceleration on a substantially continuous basis relative to a reference frame;
providing a timer which communicates a time reference signal to the processor, the processor monitoring the acceleration signal and the time reference signal on a substantially continuous basis;
waiting for the acceleration signal to indicate low acceleration within a first low acceleration range, wherein when the acceleration signal is within the first low acceleration range for a predetermined first period of time comprising a waiting for low acceleration step and is followed by a second high acceleration signal in a second high acceleration range in a second predetermined period of time comprising a waiting for high acceleration step a fall condition is determined by the processor, wherein the processor monitors the time reference signal and the acceleration signal during a third predetermined period of time subsequent to the second predetermined period of time, whereby if the acceleration signal remains in a predetermined very low acceleration range during the third predetermined period of time comprising a calculating if the user stays immobile on the surface step, wherein the predetermined very low acceleration range comprises the acceleration signal being lower than an On The Ground acceleration Sensitivity setting during a Time To Detect On The Floor time setting and wherein the sum of the Time On The Floor periods is greater than the Time On The Floor setting then it is determined that a user is immobile on the surface and a fall detection event is confirmed, and wherein a plurality of parameters of each of the first low acceleration range, the second high acceleration signal and the predetermined very low acceleration range are customized for each user with reference to personal profile settings unique to each said user and can be updated by the user.

In some embodiments, a weighting system receives input from a threshold-based algorithm and input from a machine learning model, the weighting system varying the weight applied to the respective inputs over time thereby to increase reliability of fall detection decisions.

In a further broad form of the present disclosure there is provided a detection and communication system which utilizes the above method to detect a fall condition and confirm a fall detection event, said system utilizing a method of detecting the fall event comprising: providing an accelerometer which communicates an acceleration signal to a processor, the acceleration signal quantifying acceleration on a substantially continuous basis relative to a reference frame;
providing a timer which communicates a time reference signal to the processor, the processor monitoring the acceleration signal and the time reference signal on a substantially continuous basis;
waiting for the acceleration signal to indicate low acceleration within a first low acceleration range, wherein when the acceleration signal is within the first low acceleration range for a predetermined first period of time and is followed by a second high acceleration signal in a second predetermined period of time a fall condition is determined by the processor, wherein the processor monitors the time reference signal and the acceleration signal during a third predetermined period of time subsequent to the second predetermined period of time, whereby if the acceleration signal remains in a predetermined very low acceleration range during the third predetermined period of time comprising a calculating if the user stays immobile on the surface step, wherein the predetermined very low acceleration range comprises the acceleration signal being lower than an On The Ground acceleration Sensitivity setting during a Time To Detect On The Floor time setting and wherein the sum of the Time On The Floor periods is greater than the Time On The Floor setting then it is determined that a user is immobile on the surface and a fall detection event is confirmed, said system reading a plurality of vital signs of a body of the user utilizing a sensing device in a form of a body-worn sensor and applies algorithms to interpret whether the fall detection event has occurred and then send a notification of the fall detection event with an escalation process to nominated carriers by way of a server incorporating a separate processor if the user is interpreted as having a fall, said system implemented by means of the processor associated with the body-worn sensor and the separate processor associated with the server.

In some embodiments, the sensing device may be a smartwatch or smartphone.

In some embodiments, the system may include a secured dashboard, said secured dashboard displaying user data in real time, said secured dashboard accessible to doctors or other parties via a log in sequence.

In some embodiments, the system may incorporate a memory, said memory storing user data and historical user data, said user data and said historical user data accessible to doctors or other parties for analysis via a log in sequence.

In some embodiments, the system may include a memory which retains user data relating to fall or fit or seizure episodes of each user, said memory accessible to users/patients via a login sequence thereby allowing users/patients to keep track of fall or fit or seizure episodes and monitor their progress.

In some embodiments, the transmitter may have Bluetooth or other short range radio or electromagnetic transmission capability.

In a further broad form of the present disclosure there is provided a decision system wherein reliability of decision making is improved by combining threshold-based decision making with a Machine Learning Model in order to provide an automated improvement of fall detection accuracy, said system providing acceleration data to a threshold-based algorithm, the threshold-based algorithm including personal profile settings customizable to a user, said system further including a machine learning model which receives acceleration data and learns from feedback input by the user, said system further including a weighting system which receives input from said machine learning model and from said threshold-based algorithm, said weighting system weighting input from said threshold-based algorithm more heavily than from input from machine learning model during a first phase of use by a user of the detection system, said weighting system weighting input from said machine learning model more heavily as the model learns.

In some embodiments, the system may be applied to determining whether a user has had a fall.

In some embodiments, the system may be applied to determining whether a user has had a seizure.

BRIEF DESCRIPTION OF DRAWINGS

Embodiments of the present disclosure will now be described with reference to the accompanying drawings, wherein.

DETAILED DESCRIPTION OF EMBODIMENTS

Broadly what is disclosed is a device, method and system which, in at least some embodiments, can read the vital signs of the body of a user utilizing a sensing device such as a smartwatch or smartphone (for example, utilizing the IOS, ANDROID, PEBBLE or TIZEN operating systems) and apply algorithms to interpret the vital signs and then send a notification with an escalation process to nominated carriers if the patient is interpreted as having a fall or fit or seizure. In at least some embodiments, doctors or other parties can log in to a secured dashboard and check a patient data in real time. In some embodiments, doctors or other parties can analyze the history of the patient.

In some embodiments, a plurality of parameters of each of the first low acceleration range, the second high acceleration signal and the predetermined very low acceleration range are customized for each user with reference to personal profile settings unique to each said user. In some instances, the personal profile settings unique to each said user can be updated by the user.

In at least some embodiments, users/patients can also use data to keep track of fall or fit or seizure episodes and monitor their progress.

Embodiments of the present disclosure can be applied, for example, in situations where the patient/user suffers from a medical condition, such as epilepsy, which may predispose the patient/user to falls and related events.

Figure 1A:
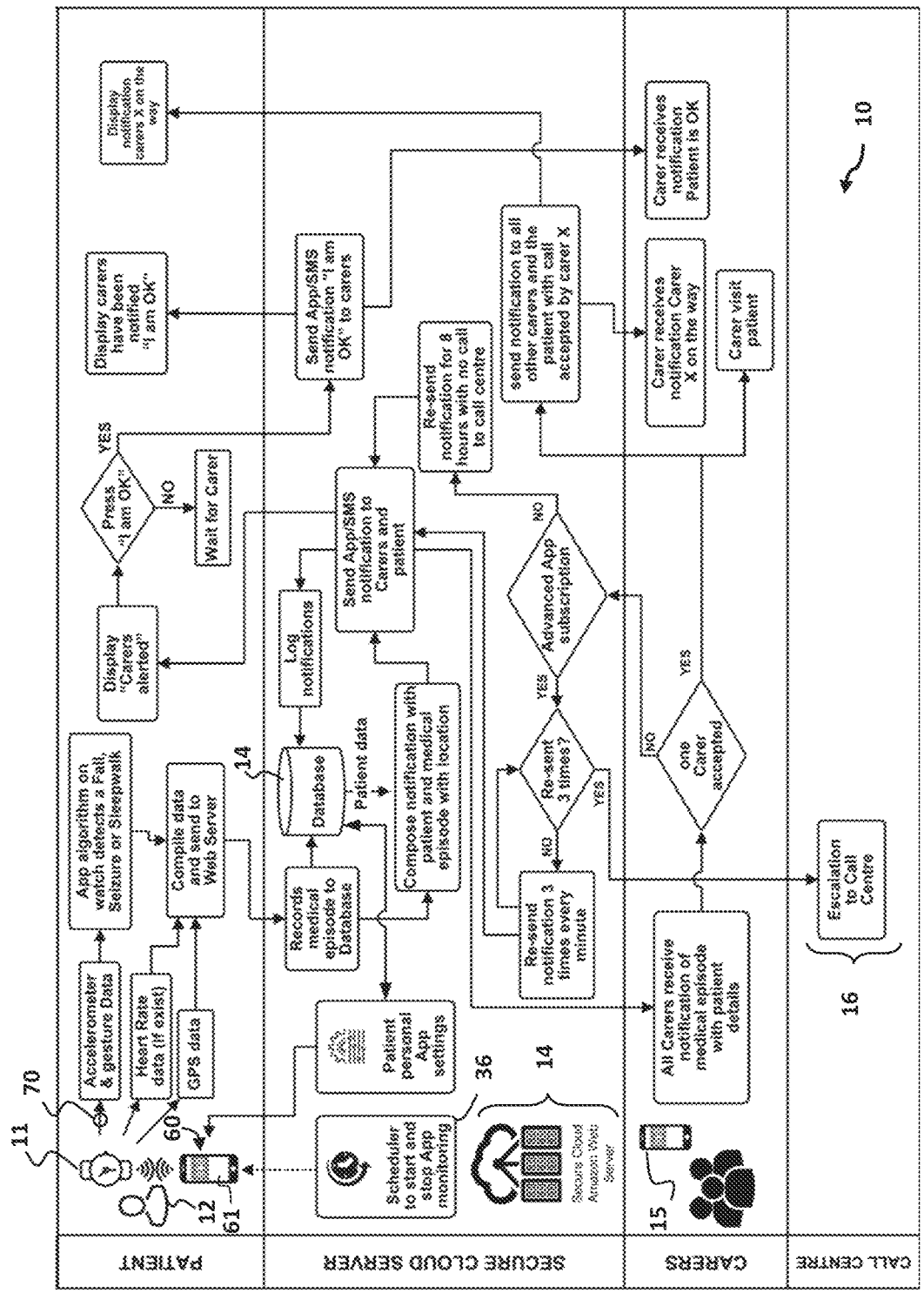
FIG. 1A is a logic flow diagram of an alert system in accordance with an embodiment of the present disclosure.
Figure 5:
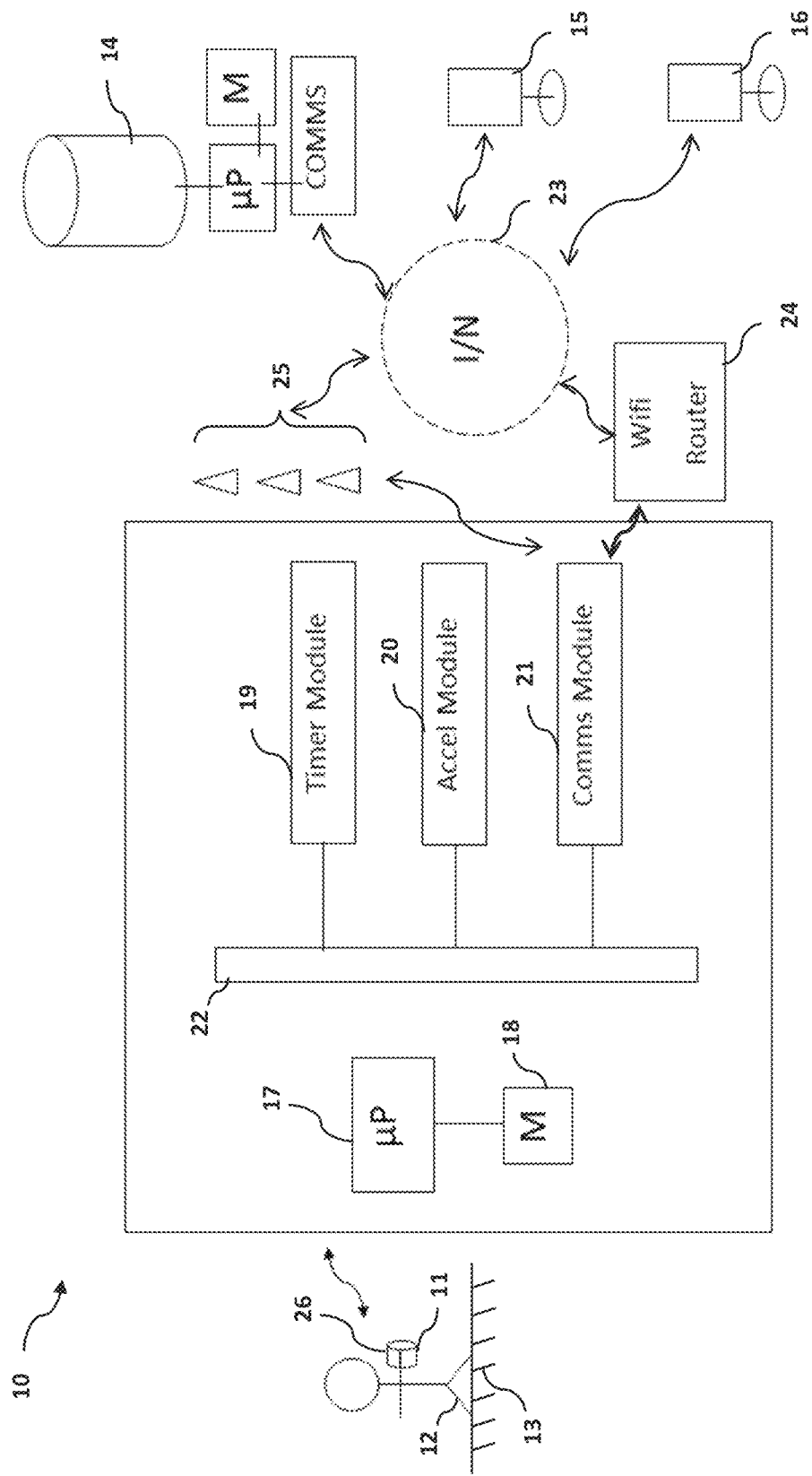
FIG. 5 is an electronic block diagram of an implementation of the system of FIG. 1A.

With reference to FIG. 1A and FIG. 5, there is illustrated an alert system 10 in accordance with a first embodiment of the present disclosure.

In this instance the alert system 10 monitors and analyzes data derived from a sensor 11. In some instances, the sensor 11 may be a body-worn sensor. In some instances, the sensor 11 may be strapped to the wrist of a user 12. In some instances, the sensor 11 may be chest-mounted, ankle-mounted or otherwise, but such that there is a mechanical association as between the sensor 11 and the body of the user 12 sufficient for the sensor to detect parameters associated with the body of the user 12.

Such parameters may include movement of the body relative to a reference frame. In some instances, the reference frame will be the surface 13 which supports the user 12.

Other parameters may include physiological parameters such as heart rate, ECG waveforms, EEG waveforms, blood pressure, blood glucose, sweat, body temperature and the like.

Figure 6:
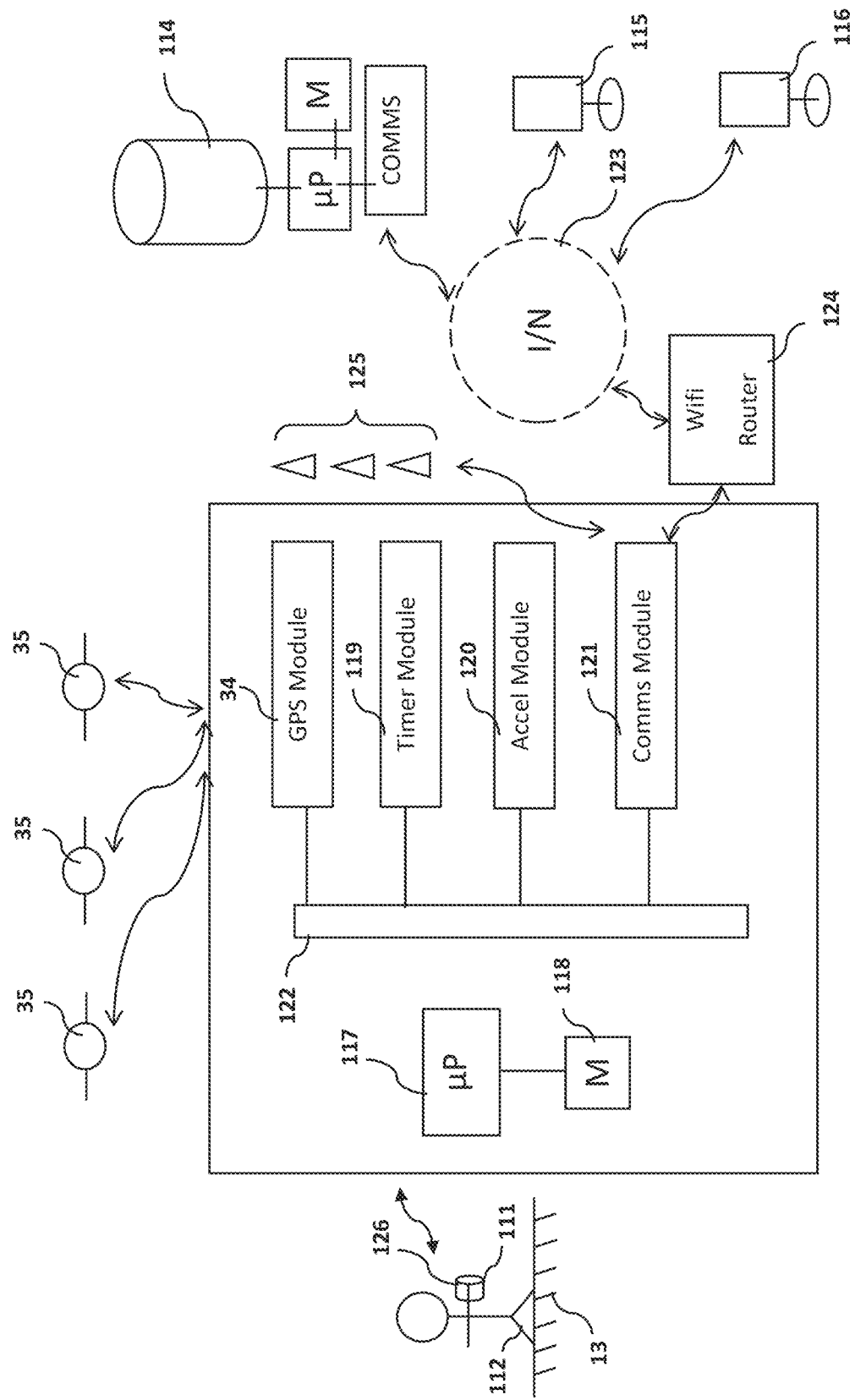
FIG. 6 is an electronic block diagram of a further implementation of the system of FIG. 1A incorporating GPS enablement.

Yet other parameters may include geographic location information and data such as is derived from a GPS module. An embodiment of the device incorporating GPS capability is shown in FIG. 6 wherein like components are numbered as for the first embodiment except in the 100 series. In this instance, in addition to time a module 119, an acceleration sensing module 120 and a communications module 121, there is included a GPS module 34 in communication with satellites 35 and, optionally, with a Wi-Fi signal as may be provided by a Wi-Fi router 124. The reference characters in FIG. 6 are designated as following:

a display 126;
a user 112;
a processor 117;
a memory 118;
a bus 122;
a cellular telephone network 125;
a server 114;
Internet 123;
a carrier digital communications device 115; and
a call center digital communications device 116.

In some embodiments the apparatus may include an accelerometer 320 which communicates an acceleration signal to a processor 117. The flow chart of FIG. 2 outlines a Threshold-Based Algorithm for determining if the user 312 has fallen with respect to the reference frame 313.

Figure 8:
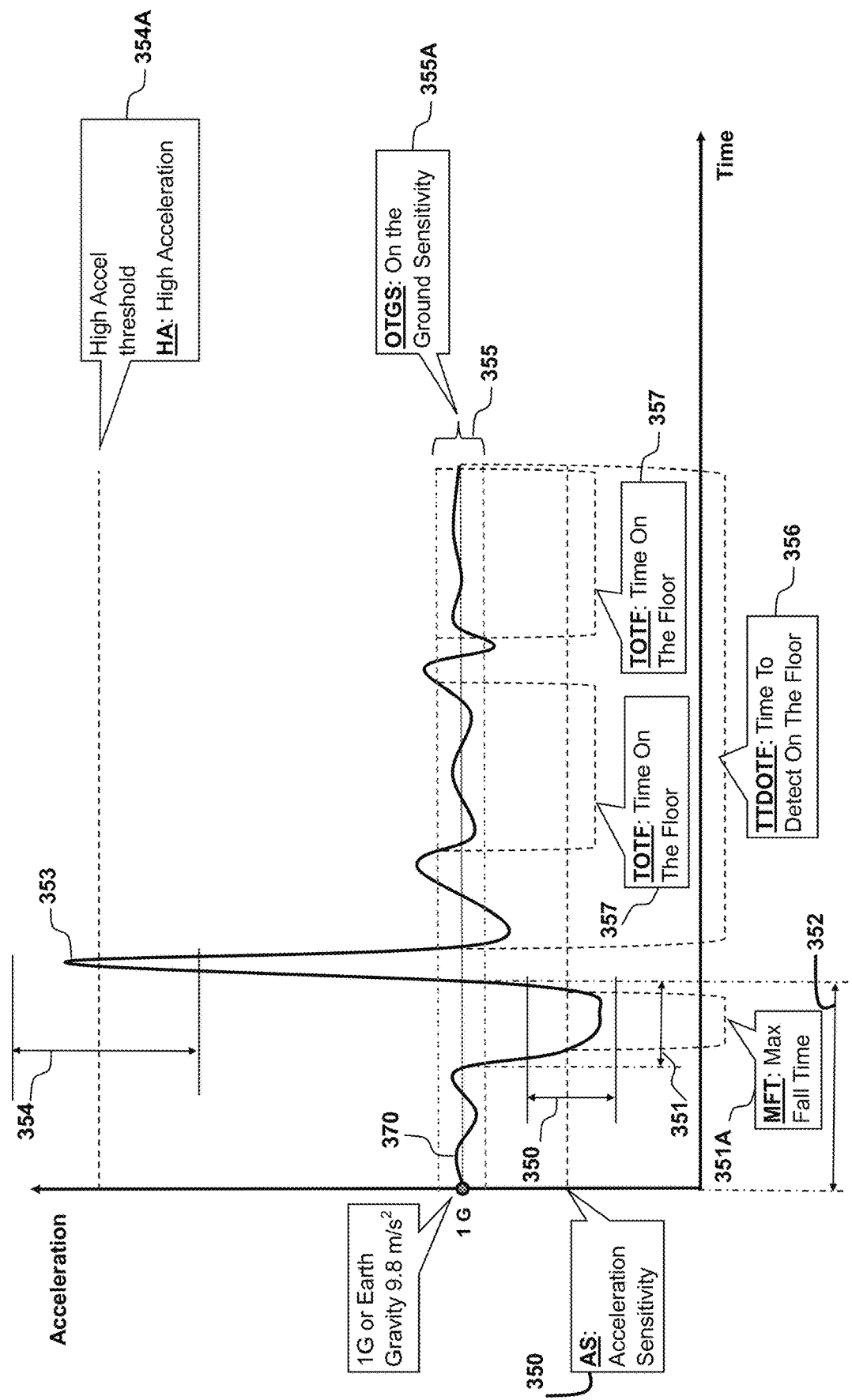
FIG. 8 is a graphical representation of a fall detection event showing the relevant time portions referenced in FIG. 2 representing acceleration over time with settings from FIG. 2.

With reference to FIG. 8, the acceleration signal 370 may quantify acceleration on a substantially continuous basis relative to a reference frame 313. A timer may communicate a time reference signal 371 to the processor. The processor may monitor the acceleration signal on a substantially continuous basis. The processor 17 may wait for the acceleration signal 370 to indicate low acceleration within a first low acceleration range when the acceleration signal has a value which remains below the user set value of AS 350A, which is within the first low acceleration range 350. In some embodiments, the value AS 350A may be in the low acceleration range 350, which is a range between 0.8 G and 0.4 G. In some embodiments, the low acceleration signal remains below the value AS 350A in the low acceleration range 350 for a longer time than the maximum fall time (MFT) value 351A. In some embodiments, the MFT 351A may be between 0.5 s to 2 s (i.e., acceleration signal 370 below AS 350A for longer than MFT 351A).

In some embodiments, having the acceleration signal is within the first low acceleration signal range 350 for a predetermined first period of time 352 is defined as a waiting for low acceleration step time 352. In some embodiments, this may be followed by a second high acceleration signal 353 in a second high acceleration range 354 which may be greater than setting HA 354A. In some embodiments, HA 354A may be an acceleration magnitude which lies in the range from 5 G to 30 G. If the signal 353 is greater than setting HA 354A, the second High Acceleration may be confirmed.

If in a second predetermined period of time comprising a waiting for high acceleration step, a fall condition is determined by the processor. The processor may monitor the time reference signal 19 and the acceleration signal 370 during a third predetermined period of time subsequent to the second predetermined period of time. If the acceleration signal 370 remains between OTGS value 355A in a predetermined very low acceleration range 355 shown in FIG. 8 during the third predetermined period of time, then the system makes the decision that a fall has occurred according to the Threshold-Based Algorithm. In some embodiments, the very low acceleration range 355 (OTGS) may be 1 G±0.3 G.

The decision as to whether a fall has occurred may comprise additional observation of the acceleration signal 370 during a Time to Detect On The Floor (TTDOTF) period 356.

The additional observation may comprise monitoring the acceleration signal during the TTDOTF period 356 such that any consecutive time periods during this period made up of shorter TOTF periods which total a predetermined amount SUM of all TOTF periods (which will be less than or equal to TTDOTF) will be interpreted that a fall has occurred.

The periods TOTF 357 may comprise time periods when the acceleration signal remains continuously within the OTGS 355 very low acceleration range. They are ended if the acceleration signal moves out of the very low acceleration range OTGS 355 at any time during the TTDOTF time period.

In the example of FIG. 8 there are two periods of TOTF within TTDOTF. Together they add to a predetermined value which the Threshold-Based Algorithm interprets as a fall condition.

In some embodiments, TTDOTF may be in the range 10 to 20 seconds. The sum of TOTF periods within this range may be set at, for example, 6 seconds. In some embodiments, a plurality of parameters of each of the first low acceleration range, the second high acceleration signal and the predetermined very low acceleration range are customized for each user with reference to personal profile settings 372 unique to each said user 312 and may be updated by the user (see FIG. 1A).

Figure 1B:
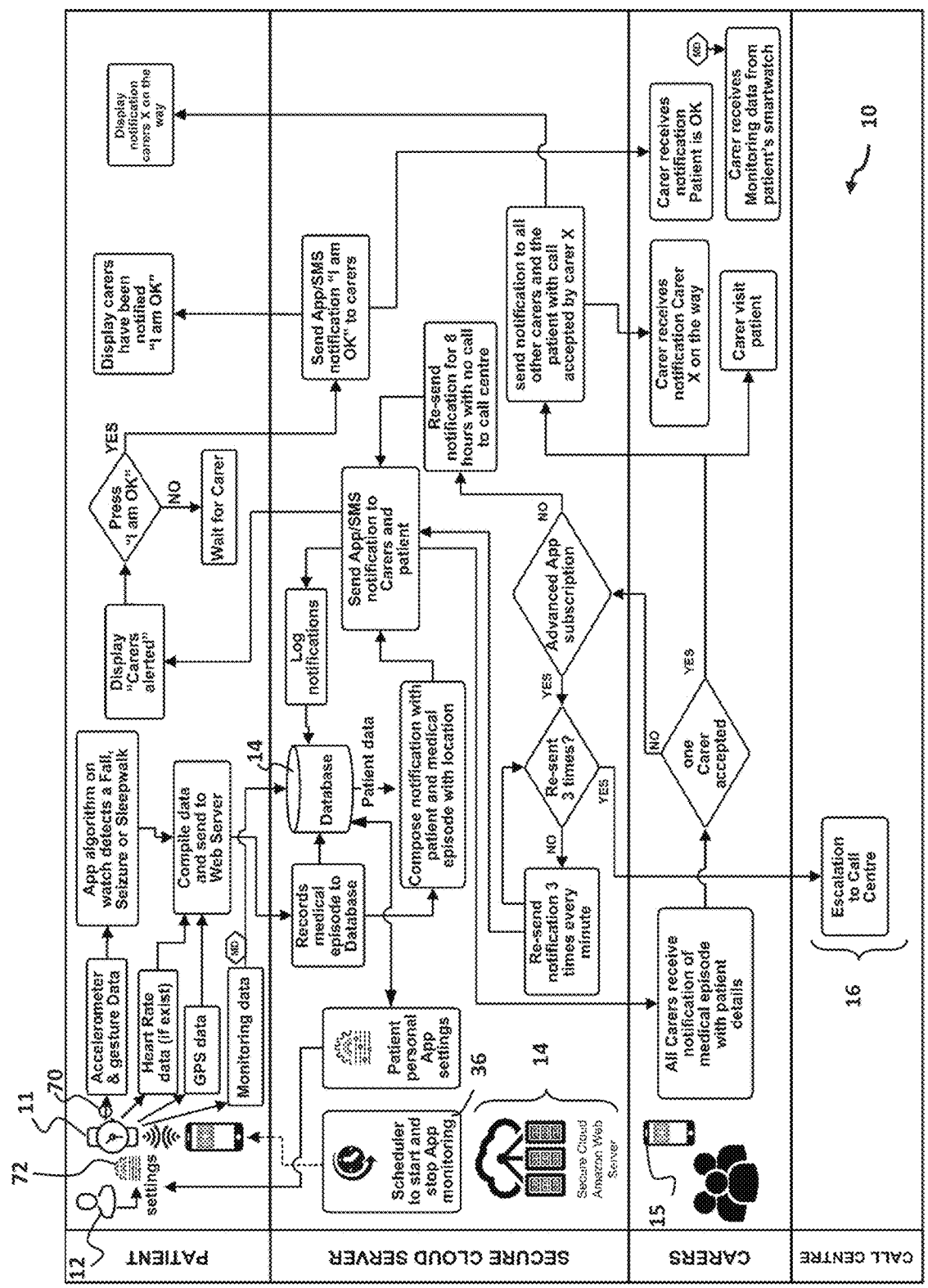
FIG. 1B is a logic flow diagram of an alert system in accordance with another embodiment of the present disclosure.

With reference to FIG. 1B, top left corner user settings 72 may be communicated to the server database 14. In some embodiments, the top left corner user settings 72 give the user full control of the customization of how the device detects falls, such as a slow fall from a chair, a hard fall from standing up, a long fall like falling from a horse, or a height of a user, etc.

Figure 2:
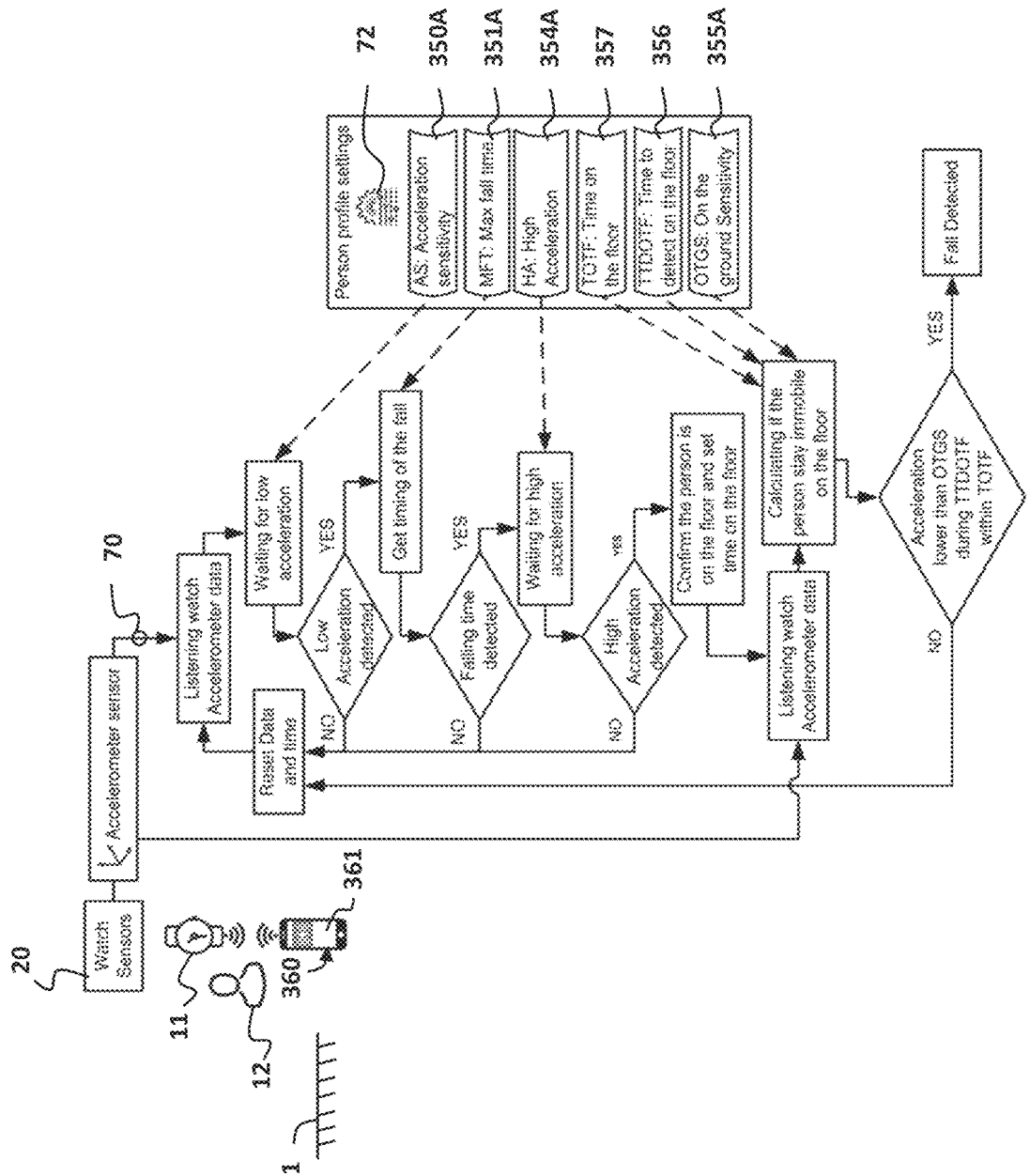
FIG. 2 is a flow chart of a fall detection algorithm applicable to the system of FIG. 1A.
Figure 9:
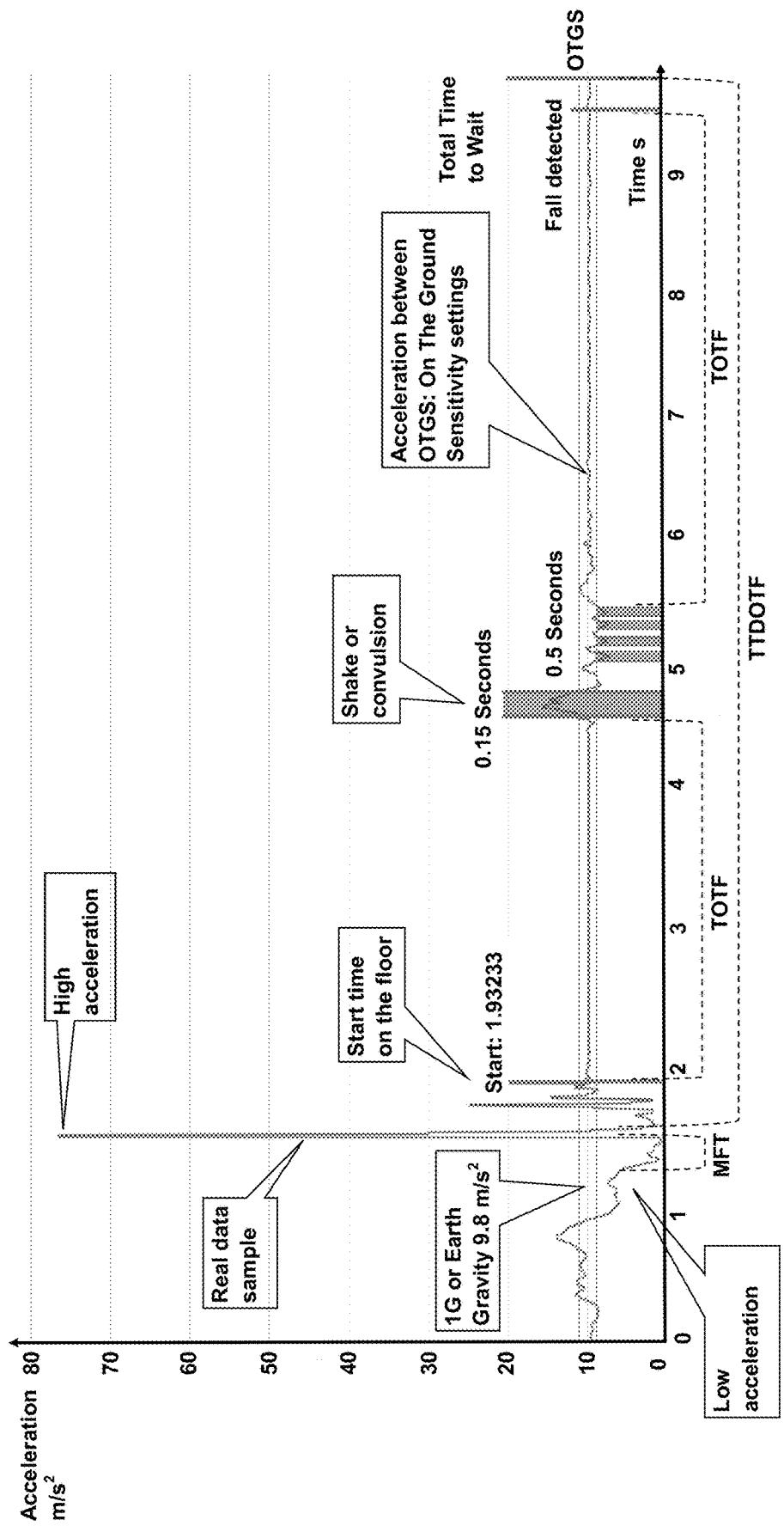
FIG. 9 is a diagram of an example of accelerometer data fed from a smart device mechanically associated with a patient in accordance with an example of fall detection applicable to FIG. 2.

A real confirmed data recorded fall is shown in the graph of FIG. 9 with reference to TTDOTF 356, TOTF 357 and OTGS 355A, as also referenced in FIG. 2. These three parameters may be used for detecting the immobility of the patient/user 312 in the third phase of a fall. The settings TTDOTF 356, TOTF 357 and OTGS 355A, are changeable by the user him/herself. In some embodiments, this may be affected through a mobile app 61 executed on a portable digital device 60, which gives the user full control of the customization of how the device detects the third phase of the fall as immobility on the floor. For example, people may have a lot of convulsions or shaking after a fall when on the floor. Alternatively, they may exhibit long-term immobility on the floor or short-term immobility on the floor. Even a very short time may be set by the user to detect all falls with no immobility time on the floor.

With reference to FIGS. 1A and 5, in some instances the user 12 will be referred to as a patient although there will be contexts in which the alert system 10 is used whereby user 12 will be the subject of monitoring by the system 10 but the description as a "patient" may not be apt.

Broadly, the system 10 may comprise components which are networked together and which, in some instances, will be geographically separated from each other.

In some embodiments, the system 10 may include a sensor 11 mechanically associated with user 12 which is in communication with a server 14. The sensor 11 may send an acceleration signal 70 to the server 14. In some instances, the sensor and/or the server 14 may also be in communication with carrier digital communications devices 15 and also, separately, in communication with call center digital communication devices 16.

In some embodiments, the sensor 11 may be in the form of a wearable device attached to the wrist of user 12.

The sensor 11 may incorporate or may be in communication locally with a processor 17, a memory 18, a timer module 19, acceleration sensing module 20 and a communications module 21. In some embodiments, the components 17, 18, 19, 20, 21 communicate with each other over bus 22.

In a further embodiment, at least the acceleration detection module and communications module may communicate via Bluetooth or other short range radio or electromagnetic transmission capability with the other components forming the sensor 11.

In some embodiments, the acceleration sensing module 20 may be implemented as at least a three-axis accelerometer which permits acceleration to be resolved in three orthogonal axes.

The communications module 21 may communicate with the Internet 23 or other wide area network either by way of a Wi-Fi router 24 or via cellular telephone network 25, whereby the sensor 11 may be placed in data communication with server 14, carrier digital communications device 15 and call center digital communications device 16.

The system 10 may further include a scheduler 36 in some instances executed as an application on the server 14. A function of the scheduler 36 may be to start and stop monitoring effected by the sensor 11.

In some embodiments, the functionality may be to automatically start the monitoring of the application on sensor 11 in the morning and close it at night, for fall and seizure event detection. For sleepwalking event detection, it may be started at bed time and closed in the morning.

In Use

Fall or Seizure Condition Monitoring

Figure 3:
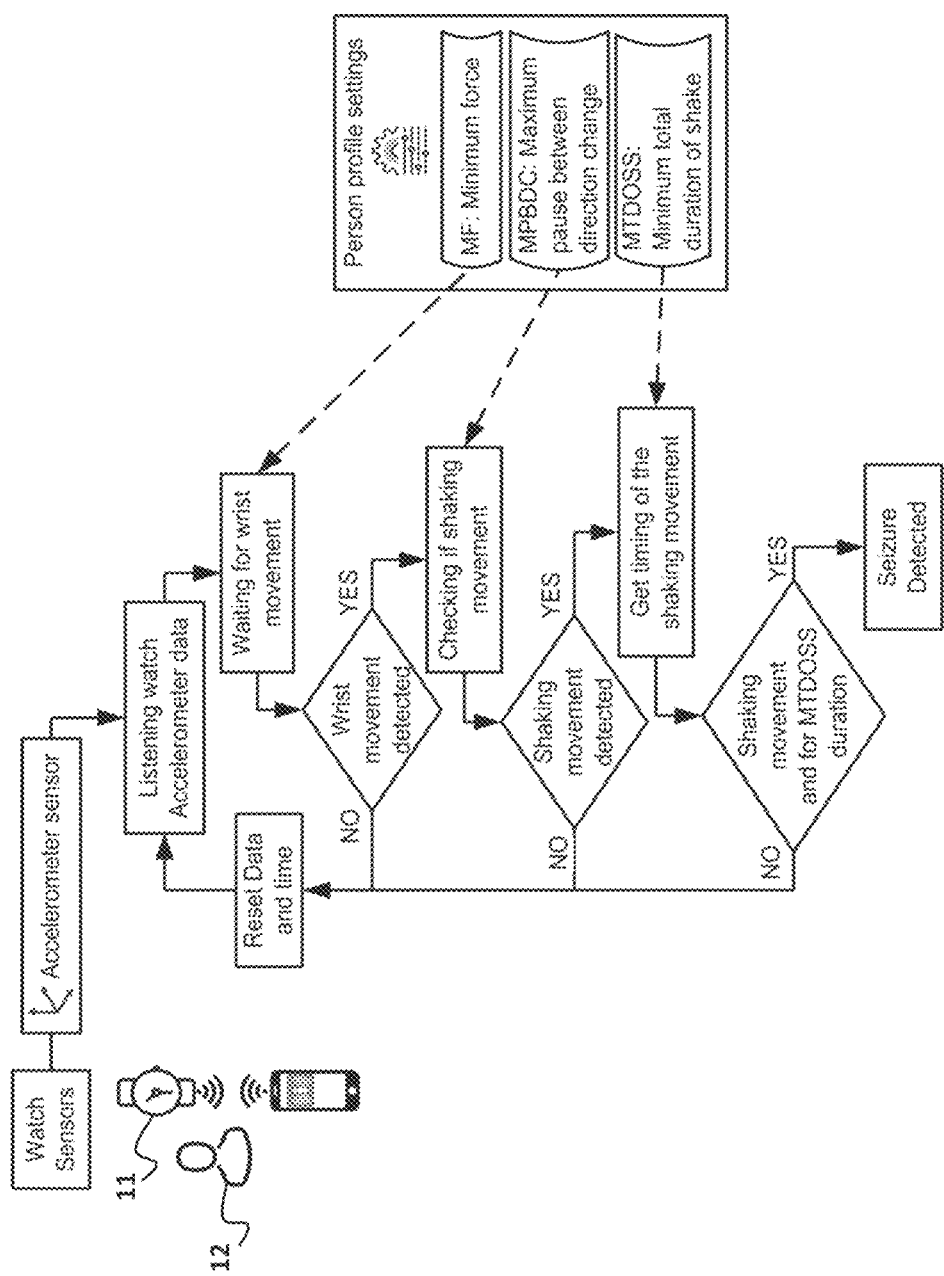
FIG. 3 is a flow chart of a seizure detection algorithm applicable to the system of FIG. 1A.
Figure 4:
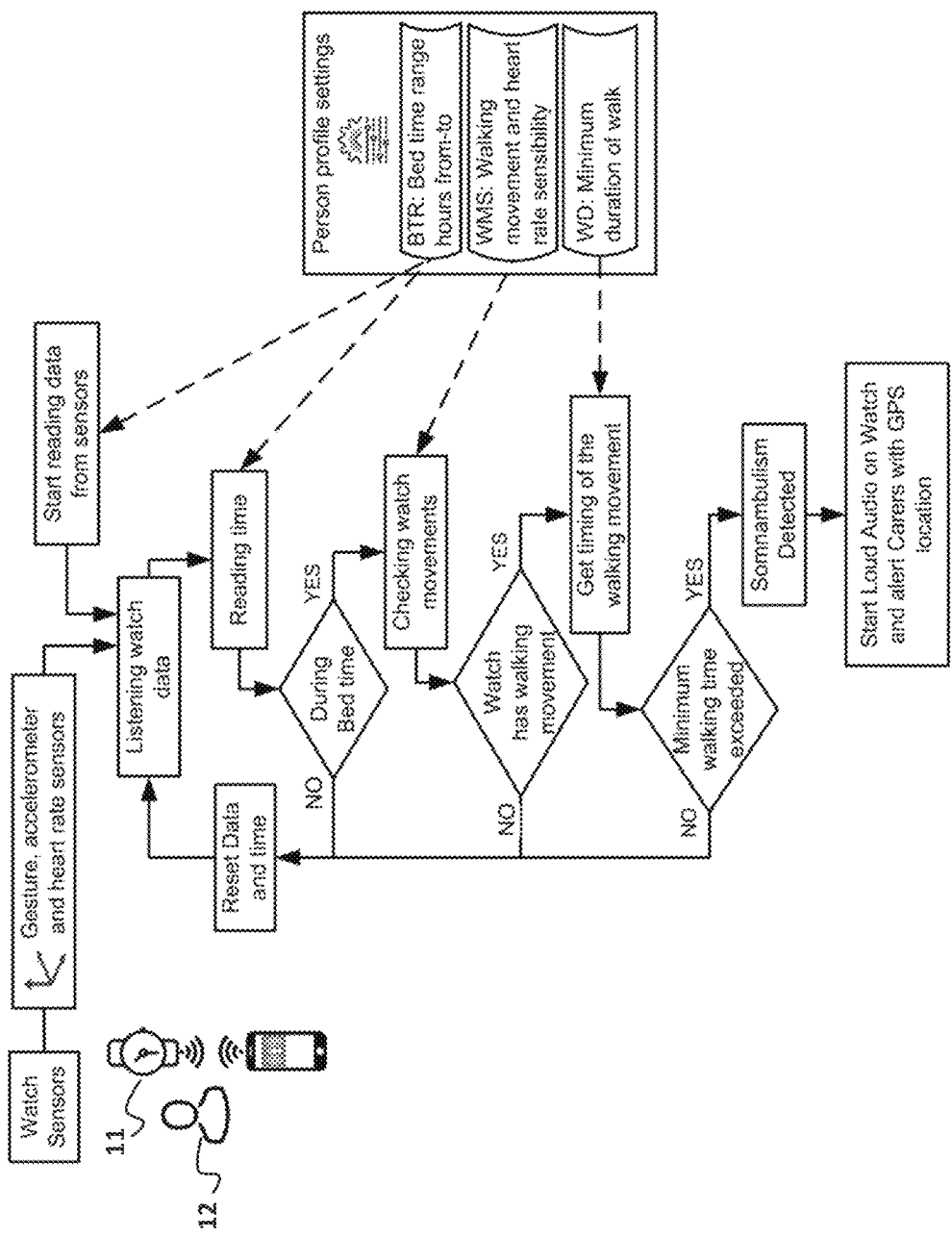
FIG. 4 is a flow chart of a sleep walk detection algorithm applicable to the system of FIG. 1A.

As seen initially in FIG. 1A, the arrangement of FIG. 5 may be utilized to monitor at least the accelerometer data and apply an algorithm referenced at least to timing data derived from timer module 19 in order to determine if a fall condition/event has occurred (as outlined in the flowchart of FIG. 2), whether a seizure event has been detected (in accordance with the flowchart of FIG. 3) or whether a sleep walk event has been detected (with reference to the flowchart of FIG. 4).

The event may then be communicated to one or more of the server 14, the carrier digital communications device 15 and the call center digital communications device 16 in accordance with the flowchart of FIG. 1A.

In some embodiments, the event may also be communicated locally to the user 12. In some embodiments, the event may be communicated locally by way of a display 26 associated with the sensor 11.

In some embodiments, the display 26 may be a touch sensitive display (or voice activation, e.g., Apple Siri or Ok Google assistance) whereby the user may communicate with one or more of the server 14, the carrier digital communications device 15 or the call center digital communications device 16.

Integrated Sensor and Communications Device

In some embodiments, the sensor 11, 111, 211, 311, or 411 may be implemented as a smartwatch app running on an independent smartwatch which has an integrated sim or esim card, such as the Apple Watch Series 3™ or the LG Urbane LTE Smartwatches™ or suitable alternative.

Machine Learning Adaptation

In some embodiments, an artificial intelligence AI capability may be programmed into memory 18 for execution by processor 17. In some embodiments, an AI program may be executed on the processor 17 associated with server 14. One particular application of the AI capability may be to learn from false positive event determination and false negative event determination in order to statistically improve reliability of detection of an event over time and with particular reference to learned attributes of the data associated with any given user 12. In some embodiments, the AI program uses Machine Learning methods works on activity recognition and analysis of the falls, such as true positive, true negative, false negative and false positive, as well as analyzing sensor data from the sensing device (smartwatch), to embed functional software changes of the parameters used by the algorithm to improve the reliability of the automatic detection personalized for each patient (user).

Figure 10:
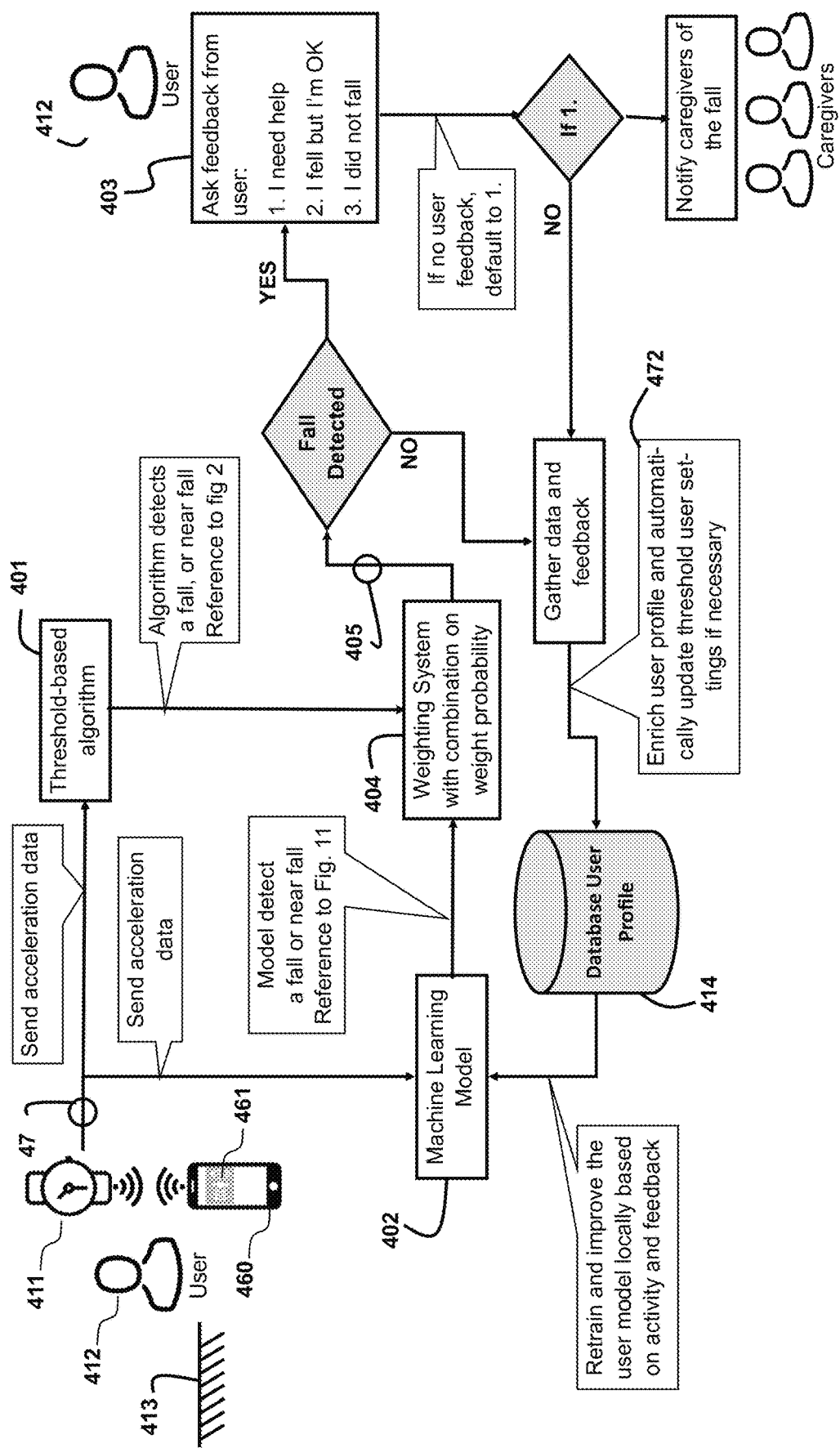
FIG. 10 is a flow chart of a data processing system according to a further embodiment where reliability of decision making is improved by combining threshold-based decision making with a Machine Learning Model in order to provide an automated improvement of fall detection accuracy.

With reference to FIG. 10, there is provided a logic flow diagram of a system which combines the probability weighting of the output of a threshold-based algorithm 401 with the output of a machine learning model 402.

The system relies on a threshold-based algorithm 401 which makes decisions as to whether a fall event has occurred based on an algorithm described in the flowchart of FIG. 2 and detailed with reference to FIGS. 8 and 9. Parameters disclosed in the flowchart of FIG. 2 may be adjusted by the user 12 (see FIGS. 1A and 1B) via the application on their smartphone or smartwatch by user settings 72. Specifically with reference to FIG. 1B, acceleration data may be sent from smartwatch 11 to the database 14. In addition, the user settings 72 (the Personal Profile Settings of FIG. 2) may also be communicated to the database 14, whereby the database 14 may monitor and act on changes made to the user settings 72. The system of FIG. 10, in addition to providing acceleration signal data to the threshold-based algorithm 401, may also provide acceleration signal data to a machine learning model 402.

The decision system 410 may receive feedback from a user as to its decisions by way of a simple question and answer prompt menu 403 which may be displayed on the smartwatch or the smartphone. When the weighting system 404 outputs that a fall has been detected, a window period may be opened to receive feedback from the user. Preferably, the weighting system receives data from a mobile app 461 executed on a portable digital device 460 providing input 470 from a Threshold-Based Algorithm (TBA) 401 and input from a Machine Learning Model (MLM) 402; the weighting system 404 varying the weight applied to the respective inputs over time thereby to increase reliability of fall detection decisions.

In the instance that the machine learning model 402 communicates that it assesses the use as having had a fall the user may respond with feedback 403 of either:

1. I need help;
2. I fell but I am okay; or
3. I did not fall, thereby allowing one way for the machine learning model to learn more regarding this user in order to increase reliability of fall detection decisions.

The decisions of the machine learning model 402 in FIG. 10 may be fed to a weighting system 404. The weighting system 404 may also receive decisions from the threshold-based algorithm 401.

Figure 12:
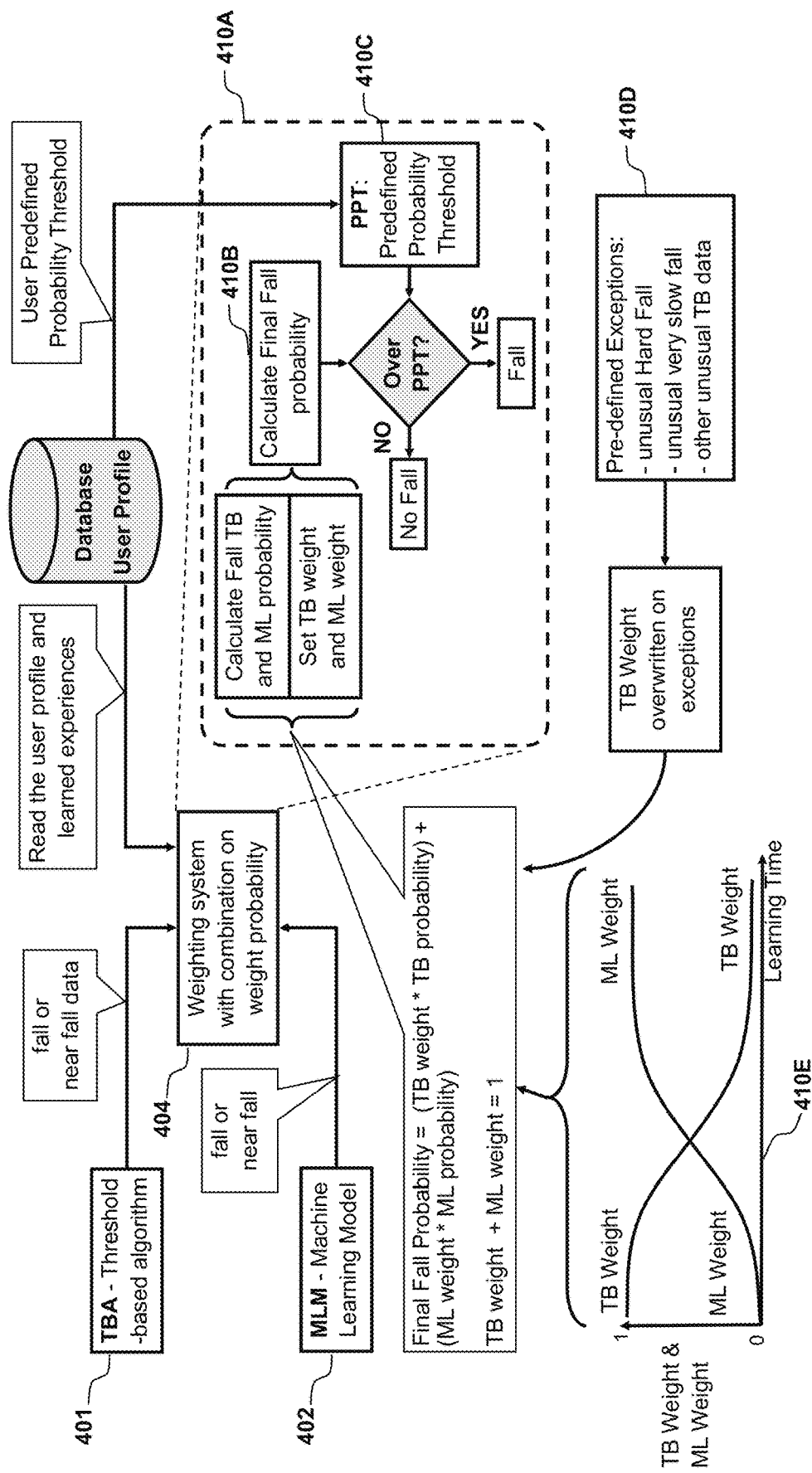
FIG. 12 is block diagram of an embodiment of the weighting system of FIG. 10.

At the time of first use by a user 12, the majority of weighting may be given to decisions of the threshold-based algorithm 401 in FIG. 12. However, as the system and the machine learning model 402 gain more learning experience as to the particular fall characteristics of that particular user and the machine learning model decisions become more reliable, the weighting system 404 may give more weight than the threshold-based algorithm 401 to the decisions of the machine learning model 402.

For example, after a few months of learning experience, the weighting given to MLM 402 may be 0.8 and to the TBA 401 it may be 0.2—wherein the weighting may be affected by time.

If TBA 401 gives a "hard fall" decision compared to MLM 402, the system 410 may give more weight to TBA 401 based on experience stored in the database-weighting affected by probability.

In both cases, the weighted determination 405 may be fed to database 414 so as to enrich the user profile 472 and automatically update threshold user settings if necessary and for final communication to carriers, as per the system illustrated in FIG. 1A and FIG. 1B.

Figure 11:
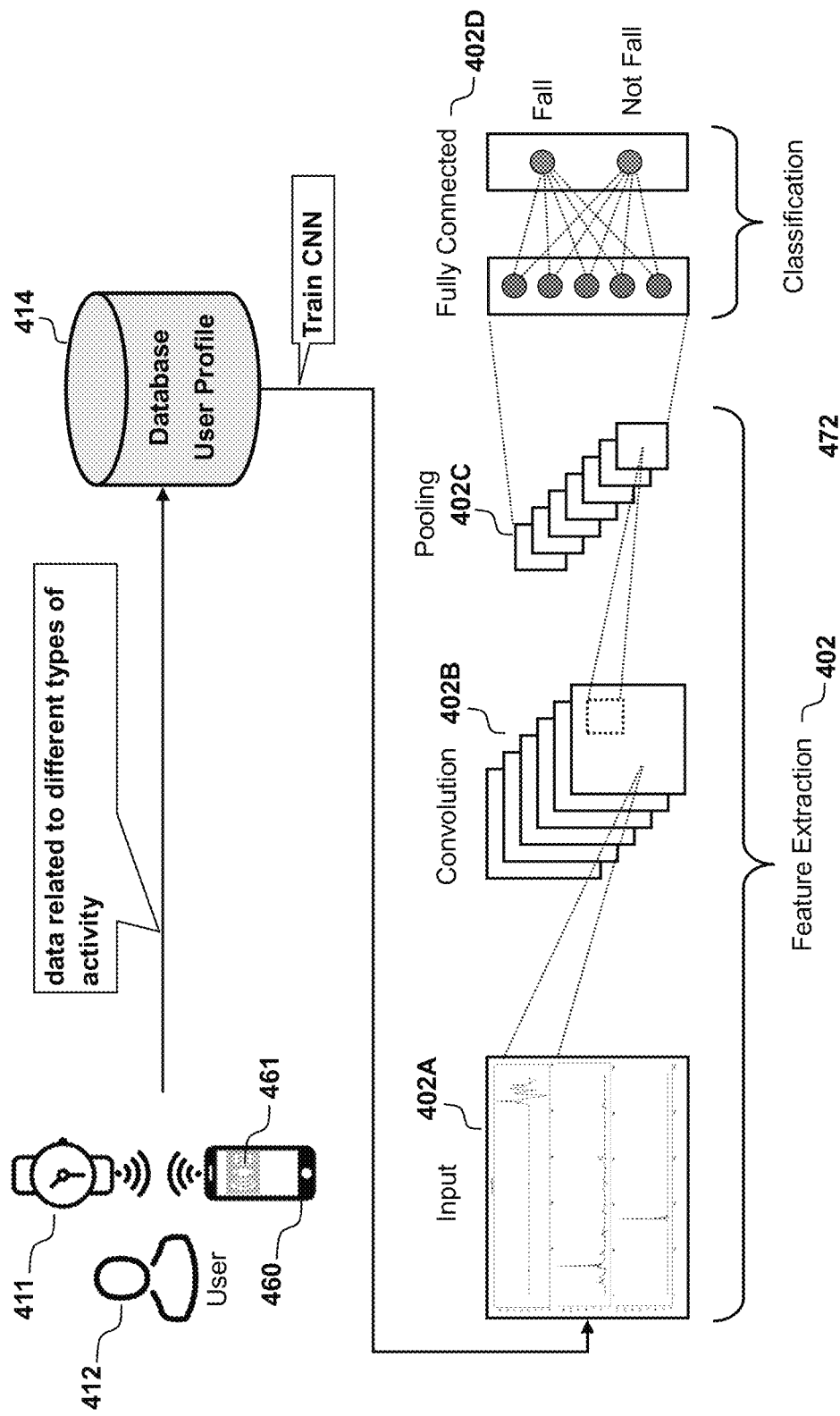
FIG. 11 is a block diagram of an embodiment of the steps which may be employed by the Machine Learning Model of FIG. 10.

With reference to FIG. 11, there is illustrated further detail of the machine learning model 402 of FIG. 10. In some instances, the machine learning model 402 may be implemented as a convolutional neural network (CNN) made up of an input step 402A, a convolution step 402B and a pooling step 402C from which the network makes a determination that either a "fall" has occurred or a "not fall" has occurred in a final classification step 402D. FIG. 11 illustrates the training steps for this machine learning model 402.

With reference to FIG. 11, deep learning methods such as convolutional neural networks (CNNs) or recurrent neural networks (RNN) have been shown to provide state-of-the-art results on challenging activity recognition tasks with little or no data feature engineering. The Machine Learning model 402 can learn an internal representation of the time-series data and ideally achieve comparable performance to models fit on a version of the dataset with engineered features. The trained model can classify inputs generated by users for different types of activity, such as walking, sitting, running, sleeping, falling, fit, etc., by capturing user activities in fixed-size time-windows and continuously sending them to the Machine Learning model 402. The CNN model can predict a probability value for each class of activity. Our research has shown that the obtained precision by the convolution model, based on CNN, over trial data is 94% with reference to FIG. 11. The model can be customized and retrained based on the target user behavior. The model can use the target user feedback to locally adjust its weights and consequently provide better results for the target users by decreasing the number of false-positive detections with reference to FIG. 10. The approach is to combine the threshold-based algorithm 401 with the deep learning approach model (MLM 402) to provide more reliable results. In some embodiments, the combined step may be performed using a weighting system 404.

With reference to FIG. 12, there is illustrated an additional detail of one embodiment of the underlying decision logic and procedure used by the weighting system 404.

In this instance, the threshold-based algorithm 401 may provide input to weighting system 404. Machine learning model 402 may also provide input to weighting system 404. Decision Logic box 410A may set out decision logic and procedure by which a "final fall probability" 410B is determined. If this value is above a Predefined Probability Threshold (PPT) threshold value 410C then a fall is determined to have occurred.

Exceptions 410D may overwrite the Threshold-Based (TB) weightings. In this instance, it will be seen in graph 410E that, over time, a higher weight is attributed to the machine learning model 402 than to the output of the threshold-based algorithm 401.

Sleep Walking Detection

With reference to FIG. 1A in conjunction with FIG. 4, instructions for an algorithm may be stored in memory 18 and executed by processor 17 operating according to the flowchart of FIG. 4 to detect and communicate and alarm, as appropriate, a sleepwalking event.

Heart Rate Monitoring Event Detection

In some embodiments, the sensor 11 may include ECG monitoring capability, whereby heart rate monitoring may provide an alert to patient and carrier when an unusual heart rate/beat is recorded.

Audio Functionality

Audio may be provided when an event such as a fall, seizure or sleepwalk is detected to alert people around and emergency services. In some embodiments, this may be affected by the sensor emitting an audible sound. In some embodiments, the sound may be loud enough for surrounding people to hear.

Sensor Condition Monitoring and Communication

The App may send notification to carriers about the App monitoring status (making sure the app is monitoring) as well as the battery level of the watch, so the carrier can contact the patient if there is any issue of the App monitoring. As reference to FIG. 1B-MD.

Integration with Other Systems-Telehealth

Figure 7:
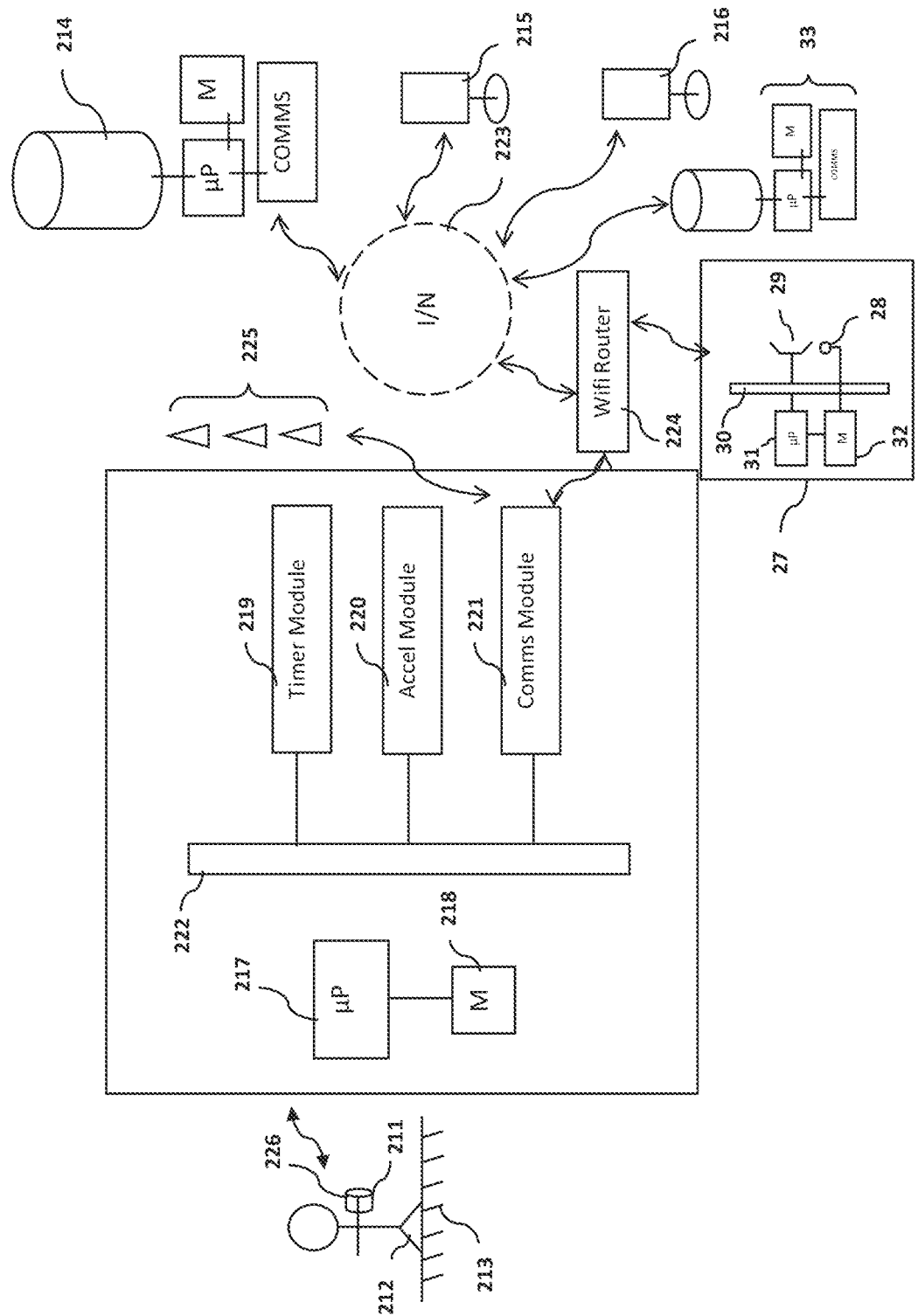
FIG. 7 is an electronic block diagram of yet a further implementation of the system of FIG. 1A facilitating telehealth and remote monitoring applications.

In some embodiments and with reference to FIG. 7, wherein like components are numbered as for the first embodiment except in the 200 series, an additional monitoring or further sensor device 27 may be located in association with user 12. In some embodiments, the additional monitoring or sensor device may be located in the home of the user or the office of the user or other location where the user may spend a predetermined period of time. The reference characters in FIG. 7 are designated as following:

a surface 213, 413;
a user 212, 412;
a display 226;
a processor 217;
a memory 218;
a timer module 219;
an acceleration sensing module 220;
a communications module 221;
a cellular telephone network 225;
a server 214;
a carrier digital communications device 215; and
a call center digital communications device 216.

The additional monitoring or sensor device 27 may include functionality and communications capability similar to that of sensor 11, but may include at least microphone 28 and, in some embodiments, speaker 29 in communication with a bus 30 which may also be in communication with processor 31 and memory 32, and therefore in communication with Wi-Fi router 224, Internet 223 and subsequently Web-enabled database 33.

In some embodiment, the additional monitoring or sensor device 27 may take the form of a smart microphone and speaker device of the form currently marketed as the Amazon Echo™, or Google™ home device or the HomePod™ from Apple.

These devices permit audio pickup typically from an entire room and also audio playback to an entire room. Third-party applications may be run on web-enabled database 33 to provide specific functionality to complement the basic functionality which can include voice recognition and giving effect to voice commands by way of communication with other devices located in the vicinity.

In some instances, this arrangement may facilitate a telehealth functionality enabling the user at home to talk to carriers and emergency workers using at least the voice recognition system built into the additional monitoring or sensing device 27. In some embodiments, an application may be loaded onto Web-enabled database 33 which, when executed, may integrate functionality of the additional monitoring or sensor device 27 with the functionality of the sensor 211.

In some instances, this combining of functionality provides a powerful, integrated body-worn sensor with a local room sensor which has at least audio pickup and audio playback capability.

INDUSTRIAL APPLICABILITY

Embodiments of the present disclosure have application wherever it is desired to monitor and communicate conditions or events associated with a user.

In some embodiments, the system may have application to fall detection and communication of the same to remote locations for the purpose of obtaining assistance or at least monitoring of the same.

In some embodiments, the system may be applied with advantage to read the vital signs of the body of a user utilizing a sensing device such as a smartwatch or smartphone (for example utilizing the IOS™, ANDROID™ or PEBBLE™ operating systems) and apply algorithms to interpret the vital signs and then send a notification with an escalation process to nominated carriers if the patient is interpreted as having a fall or fit or seizure. In some embodiments, doctors or other parties may log in to a secured dashboard and check patient data in real time. In some embodiments, doctors or other parties may analyze the history of the patient.

In some embodiments, users/patients may also use data to keep track of fall or fit or seizure episodes and monitor their progress.

Embodiments of the may be applied, for example, in situations where the patient/user suffers from a medical condition such as epilepsy and which may predispose the patient/user to falls and related events.

The above describes only some embodiments of the present disclosure and modifications, obvious to those skilled in the art, can be made thereto without departing from the scope of the present invention.

The invention claimed is:

1. A fall detection apparatus adapted to be worn by a user, the apparatus comprising:
a processor configured to:
receive data input comprising an acceleration signal and a time reference signal and determine a fall event from the data input;
an accelerometer configured for substantially continuous recording of the acceleration signal and communication of the acceleration signal to the processor, the acceleration signal quantifying acceleration of the fall detection apparatus relative to a reference frame; and
a timer configured for substantially continuous communication of the time reference signal to the processor;
wherein the processor is configured to implement a threshold-based algorithm comprising:
substantially continuously monitor the acceleration signal for detection of a low acceleration signal (LAS) within a low acceleration range (LAR), using the time reference signal, to compare a duration of the LAS to a predetermined first period of time, $t_1$;
substantially continuously monitor the acceleration signal for detection of a high acceleration signal (HAS) in a high acceleration range (HAR), subsequent to $t_1$, and using the time reference signal, to compare a duration of the HAS to a predetermined second period of time, $t_2$;
wherein on detection of the HAS having a duration longer than the predetermined second period of time, $t_2$, the processor is configured to generate a fall detection signal indicative of a fall by said user onto a surface;
wherein, on generation of the fall detection signal, the processor is configured to:
monitor the time reference signal and the acceleration signal during a third predetermined period of time, $t_3$, subsequent to $t_2$; and
generate a user immobile signal based on the acceleration signal remaining in a predetermined very low acceleration range (VLAR) during the third predetermined period of time, $t_3$,
wherein the processor is configured to generate the immobile signal by processes including:
initiate a Time To Detect On The Floor (TTDOTF) time setting which corresponds to $t_3$,
analyze the acceleration signal for all time during $t_3$;
measure at least one Time On The Floor (TOTF) period defined as a time period that the acceleration signal is within an On The Ground acceleration Sensitivity (OTGS) setting during the TTDOTF time setting,
exclude time segments corresponding to the acceleration signal outside the OTGS during $t_3$ before and/or after the at least one TOTF period,
confirm a fall detection event in response to the user immobile signal by the processor being configured to determine that a sum of the at least one TOTF period is greater than a TOTF setting;
customize at least one of the LAR, the HAS and the predetermined VLAR for the user with reference to personal profile settings unique to said user.

2. The fall detection apparatus of claim 1, further comprising a transmitter, and wherein when the fall detection event is confirmed by the processor a fall signal is transmitted by the transmitter to a remote location.

3. The fall detection apparatus of claim 2, wherein transmitter has Bluetooth or other short-range radio or electromagnetic transmission capability.

4. The fall detection apparatus of claim 1, wherein when the fall detection event is confirmed by the processor then the processor is further configured to communicate a fall signal locally.

5. The fall detection apparatus of claim 1, wherein the acceleration signal is referenced against the reference frame.

6. The fall detection apparatus of claim 1, wherein the reference frame is a surface upon which the user of the fall detection apparatus is supported.

7. The fall detection apparatus of claim 1, wherein the fall detection apparatus is adapted to be a wrist-mounted fall detection apparatus.

8. The fall detection apparatus of claim 1, wherein the processor is configured to use input from the threshold-based algorithm and use input of fall detection data from a trained neural network based machine learning algorithm to perform a weighting system function; the processor configured to adjust a weight in the weighting system function applied to the respective inputs over time based on user feedback including learned fall characteristics of the user over time thereby increasing reliability of fall detection decisions.

9. The fall detection apparatus of claim 1, wherein said TTDOTF excludes time when the acceleration signal is greater than the OTGS setting.

10. A method of detecting a fall event of a user with a fall detection apparatus comprising:
processing via a processor data input comprising an acceleration signal and a time reference signal and determining a fall event from the data input;
substantially continuously recording the acceleration signal and communication of the acceleration signal to the processor, the acceleration signal quantifying acceleration of the fall detection apparatus relative to a reference frame;
substantially continuously communicating the time reference signal to the processor;
using the processor configured to implement a threshold-based algorithm comprising:
substantially continuously monitoring the acceleration signal for detection of a low acceleration signal (LAS) within a low acceleration range (LAR), using the time reference signal, comparing a duration of the LAS to a predetermined first period of time, $t_1$;
substantially continuously monitoring the acceleration signal for detection of a high acceleration signal (HAS) in a high acceleration range (HAR), subsequent to $t_1$, and using the time reference signal, to compare a duration of the HAS to a predetermined second period of time, $t_2$;
wherein on detection of the HAS having a duration longer than the predetermined second period of time, $t_2$, the processor is configured to generate a fall detection signal indicative of a suspected fall by said user onto a surface;
wherein, on generation of the fall detection signal, using the processor for monitoring the time reference signal and the acceleration signal during a third predetermined period of time, $t_3$, subsequent to $t_2$; and
generating a user immobile signal based on the acceleration signal remaining in a predetermined very low acceleration range (VLAR) during the third predetermined period of time, $t_3$,
wherein the processor is configured to generate the immobile signal by processes including:
initiating a Time To Detect On The Floor (TTDOTF) time setting which corresponds to $t_3$,
analyzing the acceleration signal for all time during $t_3$;
measuring at least one Time On The Floor (TOTF) period defined as a time period that the acceleration signal is within an On The Ground acceleration Sensitivity (OTGS) setting during the TTDOTF time setting,
excluding time segments corresponding to the acceleration signal outside the OTGS during $t_3$ before and/or after the at least one TOTF period,
confirming a fall detection event in response to the user immobile signal by the processor being configured to determine that a sum of the at least one TOTF period is greater than a TOTF setting; and
customizing at least one of the LAR, the HAS and the predetermined VLAR the user with reference to personal profile settings unique to said user.

11. The method of claim 10, further comprising using the processor to use input from the threshold-based algorithm and use input of fall detection data from a trained neural network based machine learning algorithm to perform a weighting system function, and adjusting a weight in the weighting system function applied to the respective inputs over time based on user feedback including learned fall characteristics of the user over time thereby to increase reliability of fall detection decisions.

* * * * *